US010062165B2

(12) United States Patent
Nakaya et al.

(10) Patent No.: US 10,062,165 B2
(45) Date of Patent: Aug. 28, 2018

(54) IMAGE PROCESSING DEVICE

(71) Applicant: SHIMADZU CORPORATION, Kyoto (JP)

(72) Inventors: Tomohiro Nakaya, Kyoto (JP); Daisuke Notohara, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 7 days.

(21) Appl. No.: 15/520,450

(22) PCT Filed: Oct. 29, 2014

(86) PCT No.: PCT/JP2014/078805
§ 371 (c)(1),
(2) Date: Apr. 20, 2017

(87) PCT Pub. No.: WO2016/067399
PCT Pub. Date: May 6, 2016

(65) Prior Publication Data
US 2017/0316563 A1 Nov. 2, 2017

(51) Int. Cl.
G06T 7/70 (2017.01)
G06T 7/00 (2017.01)
(Continued)

(52) U.S. Cl.
CPC .......... *G06T 7/0012* (2013.01); *A61B 6/505* (2013.01); *A61B 6/5211* (2013.01); *G06T 7/12* (2017.01);
(Continued)

(58) Field of Classification Search
CPC ......... G06T 7/0012; G06T 2207/30008; G06T 2207/10116; G06T 7/60;
(Continued)

(56) References Cited

U.S. PATENT DOCUMENTS 5,602,935 A * 2/1997 Yoshida .................. A61B 6/505
382/132
9,922,418 B2 * 3/2018 Nakaya .................. G06T 7/0012
(Continued)

FOREIGN PATENT DOCUMENTS

JP 2004-509722 4/2004
WO WO 02/27635 4/2002
WO WO 2012/118109 7/2012

OTHER PUBLICATIONS

PCT/JP2014/078805, ISR and Written Opinion, dated Dec. 9, 2014, 6 pages—Japanese; pages—English.

*Primary Examiner* — Jingge Wu
(74) *Attorney, Agent, or Firm* — Andrew F. Young, Esq.; Lackenbach Siegel, LLP

(57) ABSTRACT

A borderline extraction element 15 extracts a borderline B of adjacent vertebrae from an X-ray image on which multiple vertebrae are projected connected in a line. A vertebral area setting element 17 sets a area sandwiched by the adjacent borderlines B as a vertebral area and an area number is put to the respective vertebral areas L. When the vertebral areas are erroneously set up, a setup data erase element 21 erases the data of the vertebral areas L and the area number when the borderline is corrected. The setup data are erased, so that the borderline B can be shift-corrected to any location. A vertebral area setting element 17 resets the vertebral area L based on the location of the corrected borderline. Accordingly, the respective vertebral areas L are set up to the accurate locations and only the borderline B extracted to the wrong location is shift-corrected and the vertebral areas are reset. The work-burden to the operator for setting the vertebral area can be largely lessened.

4 Claims, 12 Drawing Sheets

(51) Int. Cl.
*A61B 6/00* (2006.01)
*G06T 7/12* (2017.01)

(52) U.S. Cl.
CPC .............. *G06T 2207/10116* (2013.01); *G06T 2207/30012* (2013.01)

(58) Field of Classification Search
CPC . G06T 2207/20044; G06T 2207/30012; G06T 7/74; G06T 7/248; G01S 17/08; G01S 17/023; G01S 17/58; G01S 17/66; G01S 17/88; G06K 9/00805
See application file for complete search history.

(56) References Cited

U.S. PATENT DOCUMENTS

| | | | | |
|---|---|---|---|---|
| 2005/0113663 | A1* | 5/2005 | Tamez-Pena | A61B 5/055 600/407 |
| 2007/0031015 | A1* | 2/2007 | Chen | G06T 7/0012 382/128 |
| 2009/0226060 | A1* | 9/2009 | Gering | G06T 7/11 382/128 |
| 2009/0297012 | A1* | 12/2009 | Brett | G06K 9/6209 382/132 |
| 2010/0145898 | A1* | 6/2010 | Malfliet | G06T 7/0012 706/47 |
| 2013/0089253 | A1* | 4/2013 | Chabanas | G06T 17/30 382/131 |
| 2013/0322727 | A1 | 12/2013 | Goto | |
| 2015/0289831 | A1* | 10/2015 | Sakaguchi | A61B 6/5205 600/431 |
| 2016/0203598 | A1* | 7/2016 | Nakaya | A61B 6/482 382/132 |
| 2016/0242852 | A1* | 8/2016 | Yosibash | G06T 17/20 |

* cited by examiner

*FIG. 4A* *FIG. 4B* *FIG. 4C*
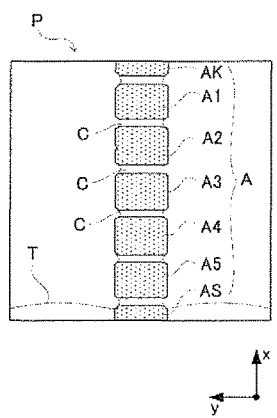
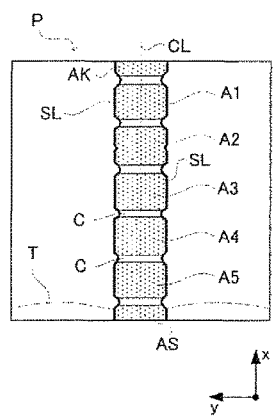
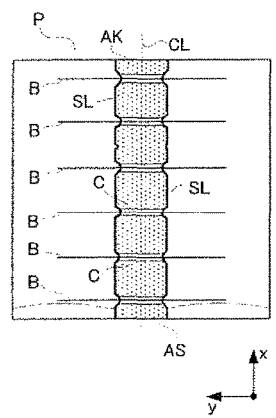

IMAGE PROCESSING DEVICE

CROSS REFERENCE TO RELATED APPLICATIONS

This application relates to, and claims priority from Ser. No.: PCT/JP2014/078805 filed Oct. 29, 2014, the entire contents of which are incorporated herein by reference.

BACKGROUND OF THE INVENTION

Field of the Invention

The present invention relates to an image processing device that performs an image processing on a medical image as an example therefor, and particularly relates to a technology related to the image processing for segment-displaying accurately a target vertebra relative to especially respective vertebral areas.

Description of the Related Art

Bone densitometry for the data to diagnose an osteoporosis and so forth may be carried out in a medical practice. When the bone density is measured, an X-ray imaging is performed using an X-ray imaging apparatus, e.g., a Dual Energy X-ray Absorptiometry (DXA). Specifically, the X-ray is irradiated to the subject in a prone position and an X-ray image of the target region of e.g., bone tissue including vertebrae and so forth is taken. And the bone density is calculated using the content of minerals contained in the bone as a benchmark based on the obtained X-ray image.

It is necessary to obtain an accurate area (size) of the individual vertebra appearing in the X-ray image to perform the bone densitometry in a high accurate level. And recently, the technology that conducts an image processing (automatic segmentation) by which the vertebral area relative to the X-ray image is automatically extracted and displayed (e.g., refer to Patent Document 1, 2).

A human vertebral column (spinal column) is formed with cervical vertebrae, thoracic vertebrae, lumbar vertebrae, sacrum and so forth, of which a number of vertebrae are continuously connected along the body axis. In addition, an intervertebral space (intervertebral disc) between the vertebrae adjacent each other exists. Generally, when the bone densitometry is performed, each vertebra from the first lumbar vertebra until the fourth lumbar vertebra among the five lumbar vertebrae is the target vertebra subject to the measurement. Therefore, according to the conventional example, an X-ray image of the lumbar vertebra of the subject is taken as a target region. And the automatic segmentation is performed on the X-ray image incorporating each lumbar vertebra and the area of each vertebra from the first lumbar vertebra to the fourth lumbar vertebra are extracted and displayed.

Hereinafter, the inventor sets forth an operation of the automatic segmentation relative to the conventional image processing device. First, referring to FIG. 10, an X-ray image P, in which the respective vertebrae A from the first lumbar vertebra A1 to the fifth lumbar vertebra A5 appear, is acquired (Step S1, FIG. 10A). Next, the image processing device detects the sideline (side profile) S of the vertebra A and the borderline B between the vertebrae A adjacent each other from the X-ray image (figure) appearing the X-ray image P. The numbers B1-B5 are assigned in order to the respective borderlines B from the head side to the foot side of the subject and the respective borderlines B are identified. For example, the borderline B1 is the borderline between the thoracic vertebra K and the first lumbar vertebra A1 and the borderline B2 is the borderline between the first lumbar vertebra A1 and the second lumbar vertebra.

Following identification of the borderline B, the image processing device executes an extraction and setting of the vertebral area based on the sideline S and the borderline B (Step S3). Specifically, the area surrounded by the sideline S, the borderline B1 and the borderline B2 is extracted and the vertebral area L1 surrounding the extracted area vertebral area is set as i.e., the area surrounding the first lumbar vertebra A1 (FIG. 10C). The vertebral area L1 is, for example, a rectangular area and the upper edge and the lower edge respectively coincide with the borderline B1 and the borderline B2.

In addition, the image processing device extracts the area surrounded by the sideline S, the borderline B2 and the borderline B3 and the vertebral area L2 is set as the area surrounding the second lumbar vertebra A2. And also, the vertebral area L3 is set as the area surrounding the third lumbar vertebra A3, and the vertebral area L4 is set as the area surrounding the fourth lumbar vertebra A4. The respective setup vertebral areas L1-L4 having the sign L1-L4 are superimpose-displayed in the X-ray image P. The respective vertebral areas L1-L4 are areas that segment individually the vertebra A having the corresponding sign among the first vertebra A1 to the fourth vertebra A4. The operator can confirm quickly the position of the respective vertebrae from the first vertebra A1 to the fourth vertebra A4 by referring the vertebral areas L1-L4 displayed automatically on the X-ray image P.

RELATED PRIOR ART DOCUMENTS

Patent Document

Patent Document 1—Patent Publication JP 2004-509722 Patent Gazette
Patent Document 2—Patent Document Publication WO2012/118109

ASPECTS AND SUMMARY OF THE INVENTION

Objects to be Solved

However, according to the conventional image processing device having such structure, it is a concerned problem that an operational procedure, by which the vertebral area displayed by the automatic segmentation is corrected, becomes troublesome and complicated.

According to the image processing device, the vertebral area set by the automatic segmentation may be false and incorrect. Firstly, as one of causes by which such mis-setting of the vertebral area takes place, it is supposed that a location of the vertebra actually appearing in the X-ray image P is shifted (deviated) from a predicted location of the vertebra because the imaging range of the X-ray image is set up mistakenly. In such case, for example, referring to FIG. 10D, the vertebrae segmented by the respective vertebral areas L1-L4 are actually from the second lumbar vertebra A2 to the lumbar vertebra A5 instead of the predicted lumbar vertebrae from the first lumbar vertebra A1 to the fourth lumbar vertebra A4. Consequently, the operator actually misrecognizes the second vertebra A2 surrounded by the vertebral area L1 as the vertebra A1.

As the other cause by which such mis-setting of the vertebral area takes place, it is supposed that a constriction of the vertebra A and so forth is mis-detected as a borderline B between the vertebrae A per se. Specifically, referring to FIG. 10E, the lumbar vertebra L2 and the lumbar vertebra L3 are set up relative to the vertebra A2 when the constriction formed in the second vertebra A2 is mis-detected as the borderline B3. Therefore, the vertebra surrounded by the vertebral area L4 is actually the third vertebra A3, but the fourth vertebra A4.

When a mis-setting of the vertebral area takes place, it is required to correct the location of the borderline B using e.g., a mouse so that the number of the vertebral areas L1-L4 and the number of the lumbar vertebrae A1-A4 can correctly match each other. However, according to the aspect of the conventional image processing device, when the location of the borderline B, the borderline B to be corrected cannot structurally move to cross-over the other borderline B. Specifically, the borderline B cannot move to any location on the X-ray image P for correction.

According to the aspect of the conventional image processing device, the followings are supposed as the reason why the movable range of the borderline B is restricted. The respective vertebral areas L1-L4 are the areas segmenting the respective vertebrae A. And, for example, the vertebral area L1 is defined as the area sandwiched by the borderline B1 and the borderline B2. Specifically, the locational relationship between the set vertebral areas L1-L4 and the identified borderlines B1-B5 are respectively correlated with a morphological restriction. As a specific example, it is restricted as the range of the vertebral area L1 varies depending on the shift of the borderline B1 or the borderline B2.

When the location of the borderline B subject to shift-correction cross-over the other borderline B, the ranges of the different vertebral areas each other per se would be overlapped because the vertebral area and the borderline are correlated each other. In such case, such incident is contradictory to the precondition in which the vertebral area is the area that individually segments the respective vertebrae. Accordingly, it is supposed that the conventional device basically prohibits that one borderline B moves to cross-over the other borderline B, or one borderline B moves to the location crossing the other borderline B.

Hereinafter, the inventor specifically sets forth the problem due to the conventional art when the borderline B4 is selected as the borderline B as an example of shift-correction. In such case, the movable range of the borderline B4 is restricted in the range, indicated by the sign F, between the borderline B3 and the borderline B5 (FIG. 11A,11B). Specifically, since at least the range of the vertebral area L3 and the range of vertebral area L4 are overlapped, the locational relationship, in which the vertebral areas L1-L4 are in order, is disrupted, so that the borderline B4 cannot move upward beyond the borderline B3 or downward beyond the borderline B5 (FIG. 11C).

Accordingly, referring to FIG. 10D, if the vertebral areas L1-L4 are actually indicating the lumbar vertebrae A2-A5, the borderline B must be shifted and corrected so that the vertebral areas L1-L4 cannot overlapped each other. In such case, first the borderline B1 is selected and shift-corrected to be in-place in the right location to correct the location of each vertebral area (FIG. 12A) and further the borderline B2, . . . , B5 are seriatim selected in order and shift-corrected respectively (FIG. 12B-FIG. 12D). As all borderlines B1-B5 must be seriatim selected and shifted in turn, the operational procedure becomes troublesome and complicated. Consequently, not only the work-burden of the operator increases, but also time needed for the image processing gets longer.

Considering such circumstances, the object of the present invention is to provide an image processing device can set the target vertebra, including the location and the range of the vertebral area, to be accurately segmented-displayed.

Means for Solving the Problem

The present invention constitutes the following structure to solve such problems.

Specifically, an image processing device of the present invention comprises: an image generation means that generates an X-ray image in which multiple concatenate bone tissues relative to a subject are projected; a borderline extraction means that extracts between borderlines of bone tissues adjacent each other relative to the X-ray image; a bone area setting means that sets up an area sandwiched by the adjacent borderlines as a bone area; a correction directive means that inputs a correction directive to correct a location of the borderlines; a setup data erase means that cancel a restriction that is each other's locational relationship between the bone area and the borderlines and is morphologically determined based on the correction directive input to the correction directive means; a borderline correction means that shift-corrects the borderline to any location of the X-ray image under a condition in which the restriction is canceled by the setup data erase means; and a resetting directive means that inputs a resetting directive to reset the bone area relative to the bone area setting means based on the location of the borderline corrected by the borderline correction means under a condition in which the borderline correction means shift-corrected the borderline.

An image processing device according to the present invention comprises a borderline correction means that shift-corrects a borderline to any location. A borderline extraction means extracts a borderline of bone tissues adjacent each other and a bone area setting means sets an area sandwiched by the adjacent borderlines as a bone area. Specifically, each bone area is an area that segments the bone tissues of a subject.

A setup data erase means cancels a restriction that is each other's locational relationship between the bone area and the borderline and is morphologically determined based on the correction directive input to the correction directive means. A borderline correction means shift-corrects the borderlines under the condition in which the restriction that is each other's locational relationship between the bone area and the borderline and is morphologically determined is canceled. The restriction between the bone area and the borderline is canceled when the borderline is shift-correct, so that the range of the location and the size of the bone area cannot vary even when the borderline shifts. Specifically, the respective bone areas segmenting the bone tissues will not overlap by the shift-correction of the borderline, the borderline correction means can shift-corrects the borderline to any location.

The resetting directive means inputs a resetting directive to the bone area setting means under the condition in which the borderline correction means shift-corrects the borderline. The bone area setting means resets the bone area based on the location, which the borderline correction means shift-corrected, in accordance with the resetting directive. Therefore, the location and the size of the bone area can be corrected by inputting the resetting directive under the condition in which only the borderline needed to be shift-corrected is selected and shifted to any target location.

Accordingly, the number of the borderlines that need to shift can be reduced when the bone area is corrected, so that the operator can lessen a work-burden due to bone area correction. In addition, time for image processing can be shortened.

In addition, according to the image processing device of the present invention, it is preferable that the setup data erase means erases the data of the bone area, which the bone area setting means sets, based on the correction directive input to the correction directive means.

According to the image processing device of the present invention, the setup data erase means erases the data of the bone area, which the bone area setting means sets, based on the correction directive input to the correction directive means. The restriction that is each other's locational relationship between the bone area and the borderlines and is morphologically determined can be absolutely canceled by erasing the data of the bone area. Further in such case, it is avoidable that the remained data of the bone area, under the condition in which the restriction is canceled, becomes a drag. Accordingly, the location of the borderline can be more quickly and accurately corrected and the bone area can be reset.

In addition, the image processing device of the present invention comprises: an area number setting means that provides an area number to distinguish the respective bone areas relative to the respective bone areas; wherein it is preferable that the setup data erase means cancels a restriction that is each other's locational relationship among the borderlines, the bone area and the area number and is morphologically determined based on the correction directive input to the correction directive means.

The image processing device of the present invention comprises the area number setting means that puts the area number to distinguish the respective bone areas relative to the respective bone areas. The operator easily distinguishes the target bone area from other bone areas by referring the area number, so that the operator can determine the bone tissues segmented by the target bone area.

The setup data erase means cancels a restriction that is each other's locational relationship among the borderlines, the bone area and the area number and is morphologically determined based on the correction directive input to the correction directive means. The borderline correction means can shift-correct the borderline to any location of the X-ray image because the restriction that is each other's locational relationship among the borderline, the bone area and the borderline and is morphologically determined is canceled, so that the work-burden due to the bone area correction against the operator can be lessened.

In addition, according to the image processing device of the present invention, the bone tissues are preferably vertebrae.

According to the image processing device of the present invention, the bone area setting means sets the bone areas to segment the respective vertebrae. The multiple vertebrae are connecting each other in a line, so that the vertebrae are suitable bone tissues for bone densitometry. Accordingly, the respective vertebrae can be segmented quickly and accurately by the bone areas by applying the image processing device of the present invention. Accordingly, the image processing suitable for bone densitometry can be quickly accomplished.

Effect of the Invention

An image processing device according to the present invention comprises a borderline correction means that shift-corrects a borderline to any location. A borderline extraction means extracts a borderline of bone tissues adjacent each other and a bone area setting means sets an area sandwiched by the adjacent borderlines as a bone area. Specifically, each bone area is an area that segments the bone tissues of a subject.

A setup data erase means cancels a restriction that is each other's locational relationship between the bone area and the borderline and is morphologically determined based on the correction directive input to the correction directive means. A borderline correction means shift-corrects the borderline under the condition in which the restriction that is each other's locational relationship between the bone area and the borderline and is morphologically determined is canceled. The restriction between the bone area and the borderline is canceled when the borderline is shift-correct, so that the range of the location and the size of the bone area cannot vary even when the borderline shifts. Specifically, the respective bone areas segmenting the bone tissues will not overlap by the shift-correction of the borderline, the borderline correction means can shift-corrects the borderline to any location.

The resetting directive means inputs a resetting directive to the bone area setting means under the condition in which the borderline correction means shift-corrects the borderline. The bone area setting means resets the bone area based on the location, which the borderline correction means shift-corrected, in accordance with the resetting directive. Therefore, the location and the size of the bone area can be corrected by inputting the resetting directive under the condition in which only the borderline needed to be shift-corrected is selected and shifted to any target location. Accordingly, the number of the borderlines needed to be shifted can be reduced when the bone area is corrected, so that the operator can lessen a work-burden due to bone area correction. In addition, time for image processing can be shortened.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 4A-FIG. 4C are schematic diagrams illustrating a processes of the Step S1 and the Step S2 according to the aspect of the Embodiment.

FIG. 4A is a schematic diagram illustrating an X-ray image generated at the step S1; FIG. 4B is a schematic diagram illustrating sidelines extracted at the step S2; and FIG. 4C is a schematic diagram illustrating borderlines extracted at the step S2.

FIG. 7A is a schematic diagram illustrating the condition in which an extraction error relative to the borderline takes place;

FIG. 7B is a schematic diagram illustrating vertebral areas set based on the borderline when the extraction error takes place; and FIG. 7C is a schematic diagram illustrating area numbers given to the vertebral areas at which the setting error take place.

FIG. 8A is a schematic diagram illustrating selection of the borderline and erase of the setup data at the step S5;

FIG. 8B is a schematic diagram illustrating a correction process of the location of the borderline at the step S6;

FIG. 8C is a schematic diagram illustrating vertebral areas reset based the location of the borderline following the correction; and FIG. 8D is a schematic diagram illustrating area numbers reput to the reset vertebral areas.

FIG. 9A is a schematic diagram illustrating an execution of cancellation of the selection of the borderline, and the restriction that is each other's locational relationship between the borderline and the setup data and is morphologically determined;

FIG. 9B is a schematic diagram illustrating a correction process of the location of the borderline at the step S6;

FIG. 9C is a schematic diagram illustrating vertebral areas reset based on the location of the borderline following the correction, and the repot area numbers thereon.

FIG. 10A is a schematic diagram illustrating the X-ray image generated according to the conventional example;

FIG. 10B is a schematic diagram illustrating borderlines extracted from the X-ray image according to the conventional example; FIG. 10C is a schematic diagram illustrating the vertebral areas set according to the conventional example;

FIGS. 10D, 10E are schematic diagrams illustrating an example of a setting error occurred in the conventional Example relative to vertebral areas.

FIG. 11A is a schematic diagram illustrating a movable range of the borderline;

FIG. 11B is a schematic diagram illustrating the case in which the borderline can be shift-corrected; and FIG. 11B is a schematic diagram illustrating the case in which the borderline cannot be shift-corrected.

FIGS. 12A-12D are schematic diagrams respectively illustrating the process of shift-correction borderlines in turn.

FIG. 12A is a schematic diagram illustrating the process of shift-correction borderline B1;

FIG. 12B is a schematic diagram illustrating the process of shift-correction borderline B2;

FIG. 12C is a schematic diagram illustrating the process of shift-correction borderline B3; and FIG. 12D is a schematic diagram illustrating the process of shift-correction borderline B5.

DETAILED DESCRIPTION OF THE PREFERRED EMBODIMENTS

Figure 1:
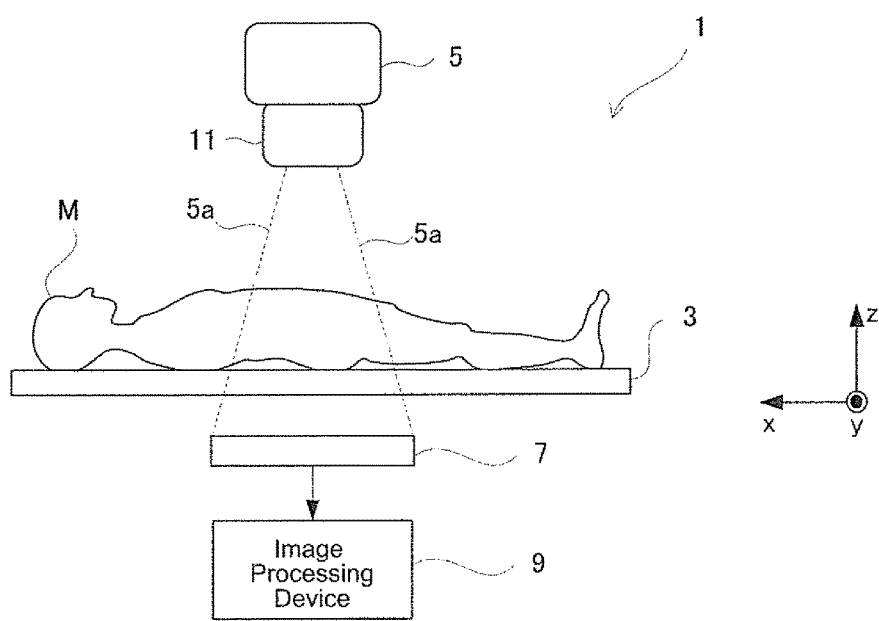
FIG. 1 is a schematic view illustrating an X-ray imaging apparatus comprising an image processing device according to the aspect of the Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Figure 2:
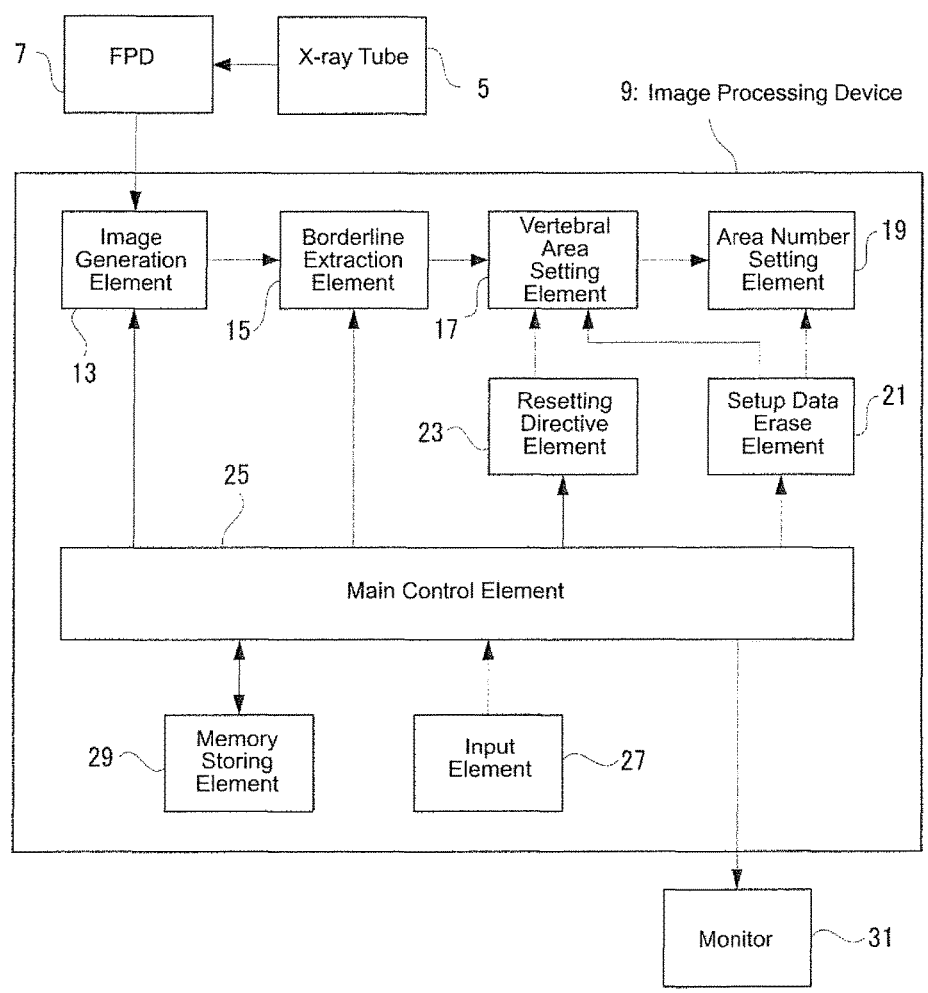
FIG. 2 is a functional block diagram illustrating an X-ray imaging apparatus comprising an image processing device according to the aspect of the Embodiment.

Referring to FIGs., the inventors sets forth the Embodiment of the present invention. FIG. 1 is a schematic view illustrating an X-ray imaging apparatus comprising an image processing device according to the aspect of the Embodiment. FIG. 2 is a functional block diagram illustrating an X-ray imaging apparatus comprising an image processing device according to the aspect of the Embodiment. Meantime, target bone tissues for an X-ray imaging according to the aspect of the Embodiment are vertebrae of the lumbar vertebra.

(Illustration of the Entire Structure)

First, the inventor illustrates an X-ray imaging apparatus 1 comprising an image processing device according to the aspect of the Embodiment. Referring to FIG. 1, an X-ray imaging apparatus 1 according to the aspect of the Embodiment 1, comprises a tabletop 3 on which a subject M is lying down (in a decubitus position), an X-ray tube 5 that irradiates an X-ray 5a to the subject M, and an FPD 7 that detects the X-ray irradiated to and transmitted through the subject M and outputs the detection signal, and an image processing device 9 that performs a variety of image processings based on the X-ray detection signals output from the FPD 7. The image processing device 9 corresponds to an image processing apparatus of the Embodiment.

The X-ray tube 5 and the FPD 7 are in-place facing each other sandwiching the tabletop 3. The FPD 7 comprises a detection surface that detects X-rays, on which surface the X-ray detection elements are 2-dimensionally arranged. The collimator 11 installed below the X-ray tube 5 limits X-rays irradiated from the X-ray tube 5 to a pyramid-like cone shape.

Referring to FIG. 2, the image processing device 9 c comprises a image generation element 13, a borderline extraction element 15, a vertebral area setting element 17, an area number setting element 19, a setup data erase element 21, a resetting directive element 23 and a main control element 25. The image generation element 13 installed in the posterior of the FPD 7 generates the X-ray image of the subject M based on the X-ray detection signal output from the FPD 7. The image processing device 9 corresponds to an image processing apparatus of the present invention. The image generation element 13 corresponds to the image generation means of the present invention.

The borderline extraction element 15 is installed in the posterior of the image generation element 13 and extracts the side profile (sideline) of a vertebra and a borderline in-between the adjacent vertebrae each other based on the X-ray figure (image) appearing in the target X-ray image. The vertebral area setting element 17 is installed in the posterior of the borderline extraction element 15 and sets vertebral areas relative to the respective vertebrae based on the sidelines and the borderlines which the borderline extraction element 15 extracts. The borderline extraction element 15 corresponds to the borderline extraction means of the present invention. The vertebral area setting element 17 corresponds to the bone area setting means of the present invention.

The area number setting element 19 is installed in the posterior of the vertebral area setting element 17 and assigns the area number distinguishing the vertebral areas respectively relative to the vertebral areas set for each vertebra. The setup data erase element 21 is installed in the anterior of both of the vertebral area setting element 17 and the area number setting element 19. The setup data erase element 21 erases the data of the already setup vertebral areas and the data of the already assigned area numbers.

The resetting directive element 23 is installed in the anterior of the vertebral area setting element 17 and sends the directive containing the contents by which the vertebral area is reset based on the location of the borderline following correction to the vertebral area setting element 17. The main control element 25, comprising a central processing unit (CPU) and so forth, controls comprehensively the respective elements such as the image generation element 13 and so forth installed in the image processing device 9. The setup data erase element 21 corresponds to the setup data erase means of the present invention. The resetting directive element 23 corresponds to the resetting directive means of the present invention.

The image processing device further comprises an input element 27, a memory storing element 29. The input element 27 to which an operator inputs a directive is e.g. a mouse, a joystick, a trackball and a touchpanel and so forth. Particularly, when the location of the borderline is corrected, the operator inputs the directive to correct the borderline by operating the input element 27 and select-and-shifts the borderline to be corrected. The input element 27 corresponds to the correction directive means and the borderline correction means of the present invention.

The memory storing element 29 stores the X-ray image generated by the image generation element 13 and the data of the vertebral area set for the X-ray image and so forth. In addition, the X-ray imaging apparatus 1 comprised a monitor 31. The monitor 31 displays not only the X-ray image, but also superimpose-displays the vertebral area set in the X-ray image to the X-ray image per se.

Description of the Operation

Figure 3:
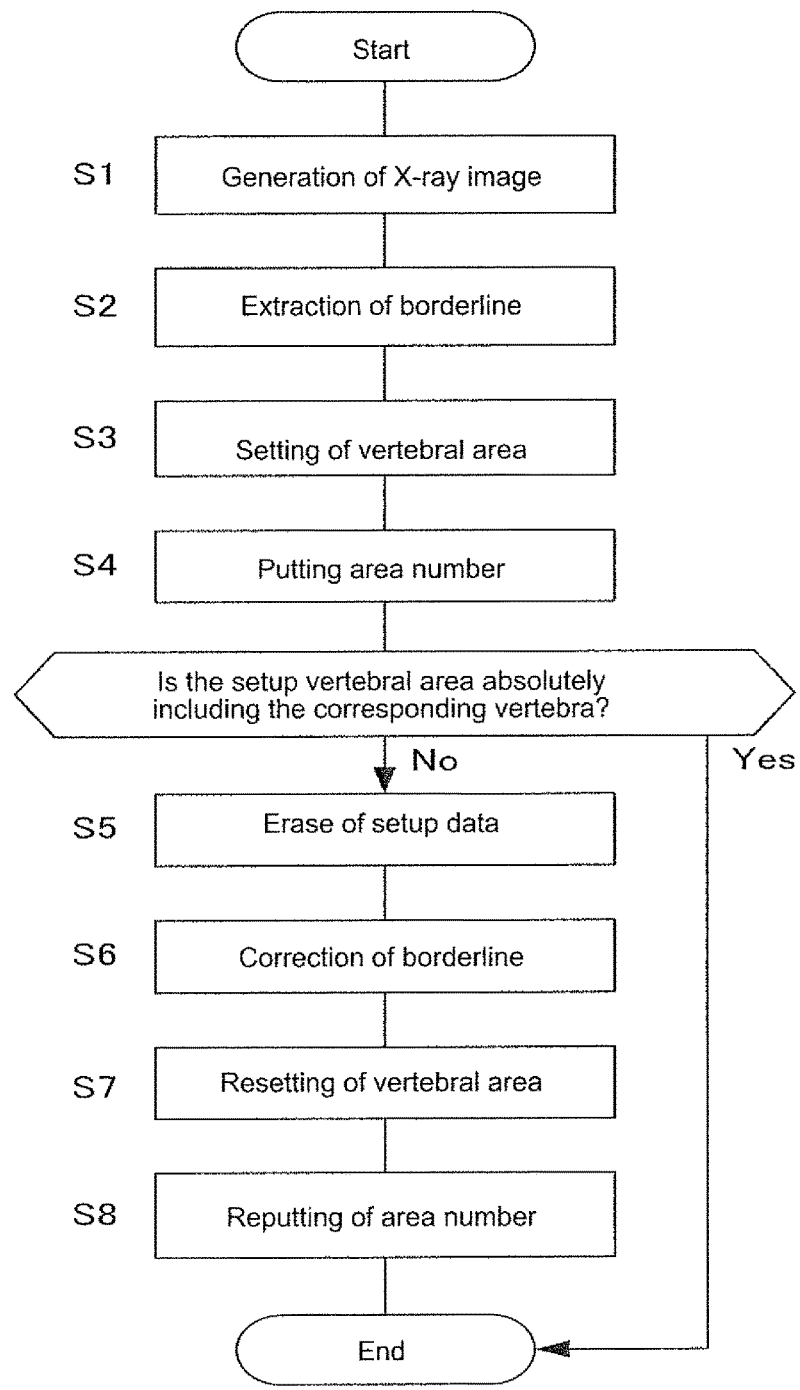
FIG. 3 is a flow chart illustrating an operation of the image processing device according to the aspect of the Embodiment.

Next, the inventor sets forth operations for an automatic segmentation relative to an X-ray image applied to bone densitometry, referring to the X-ray imaging apparatus 1 according to the aspect of the Embodiment. FIG. 3 is a flow chart illustrating an operation of the X-ray imaging apparatus 1 according to the aspect of the Embodiment. The inventor sets forth an Embodiment using a vertebra of the lumbar vertebra as a target bone tissue for bone densitometry. In addition, the automatic segmentation according to the aspect of the Embodiment automatically extracts areas from the first lumbar vertebra to the fourth lumbar vertebra. The number of the areas automatically extracted and the bone tissues as the extraction target can be changed as needed corresponding to the diagnostic condition.

Step S1 (Generation of an X-Ray Image)

First, an X-ray image which is applied to the bone densitometry is taken. The operator loads the subject M on the tabletop 3 so that the body axis direction of the subject M coincides with the x-direction (long side of the tabletop 3). Then, the operator makes sure the irradiation field of the visible light irradiated from the collimator 11 and so forth, determines the approximate imaging location (location of the imaging system) for the X-ray imaging, and shifts the X-ray imaging system comprising both X-ray tube 5 and the FPD 7 to the adequate location. According to the aspect of the Embodiment, the bone densitometry is performed based on the X-ray image of the vertebra of the lumbar vertebra, so that the imaging location corresponds to the proximity of the low back.

The operator directs the generation of the X-ray image by operating the input element 27 following shifting the respective elements of the image system. The X-ray tube 5 irradiates an X-ray 5b to the subject M based on the contents of the directive. The irradiated X-ray 5b transmits the subject M and is being detected by the FPD 7. The FPD 7 outputs an X-ray signal based on the detected X-ray. Referring to FIG. 4A, the image generation element 13 generates an X-ray image P showing the respective vertebrae A extending in the x-direction and the pelvis L based on the detected X-ray signal.

Meantime, the vertebrae of the five lumbar vertebrae as the target region among the appearing vertebrae A on the X-ray image P are discriminated by assigning the signs as the first lumbar vertebra A1 to the fifth lumbar vertebra A5. In addition, the vertebra A (thoracic vertebra) located in the head side of the first lumbar vertebra A1 is indicated by the sign AK and the vertebra A (sacral vertebra) located in the leg side of the fifth lumbar vertebra A5 is indicated by the sign AS. The generated X-ray image P is sent to the borderline extraction element 15 and also displayed on the monitor 31.

Step S2 (Extraction of a Borderline)

The borderline extraction element 15 executes an image processing to extract a borderline between adjacent vertebrae relative to the X-ray image P. The borderline extraction element 15 executes an image processing to extract the side profile (sideline) forming the profile of the vertebra A as a pre-processing for extraction of the borderline of the vertebra A. A processing method to extract the sideline is not particularly limited as far as a known method. For example, as an example of the sideline extraction processing method, it can be the method in which the sideline is extracted based on the image processed with the line thinning processing using e.g., the shrink processing relative to the morphology operation following the binarization processing, As results, two of the sidelines SL of the vertebra A extending in the x-direction are extracted by the sideline extraction processing (FIG. 4B). The borderline extraction element 15 extracts the locus of the midpoint relative to the right and left sidelines SL can be extracted as the centerline CL. The extracted center line CL represents the direction along which the respective vertebrae A are extending between the cervical vertebrae and the pelvis (x-direction of the Embodiment).

Referring to FIG. 4C, the borderline extraction element 15 extracts the borderline B of the adjacent vertebrae A following extraction processing for the sideline. An intervertebral disc space C exists between the adjacent vertebrae A. It is given that the extracted borderline B of the vertebra A according to the Embodiment coincides with the center line of the intervertebral disc space C in the direction (x-direction) in which the respective vertebrae A are concatenated. The extraction method of the borderline B is not limited to the above method and any known method can be applied. For example, the borderline B can be extracted based on the constricted location of the sideline SL of the vertebra or a contrast of brightness between adjacent vertebrae A per se. The X-ray image P having the extracted borderline B is sent to the vertebral area setting element 17.

Step S3 (Setting of a Vertebral Area)

Figure 5:
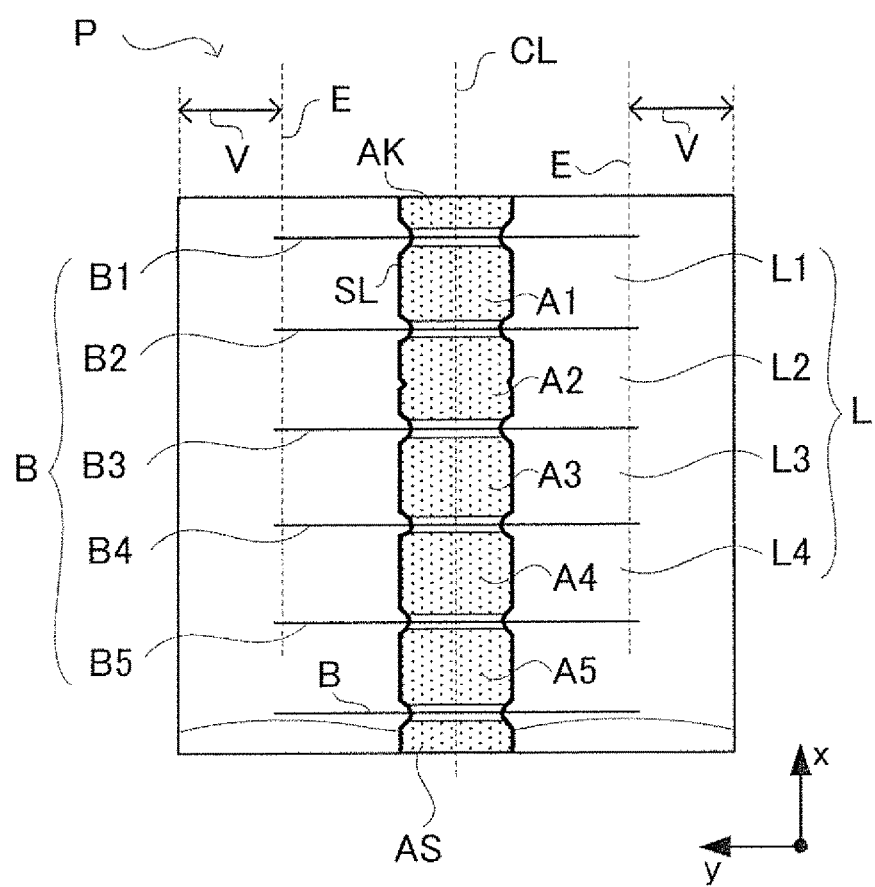
FIG. 5 is a schematic diagram illustrating a process of the Step S3 according to the aspect of the Embodiment.

The vertebral area setting element 17 sets the vertebral area based on the borderline B extracted from the X-ray image P. The vertebral area setting element 17 identifies five borderline B1-B5 located in the head side of the subject M among the multiple borderlines B as the pre-processing for setting the vertebral area. In addition, the vertebral area setting element 17 detects two lines E extending in the x-direction based on the adequate condition. As an example, of detection of the line E, the line E is extracted as a line distant by the predetermined distance V away from both right- and left-end of the X-ray image P (referring to FIG. 5). In addition, the line can be extracted as the line distant by the predetermined distant away in the y-direction (short side direction of the tabletop 3) from the center line CL.

The vertebral area setting element 17 sets the vertebral areas L1-L4 on the X-ray image P by respectively setting the area sandwiched by two adjacent borderlines B as the vertebral area. Specifically, referring to FIG. 5, the vertebral area setting element 17 sets the surrounding area by the line E, the borderline B1 and the borderline B2 as the vertebral area L1. In addition, the area surrounded by the line E, the borderline B2 and the borderline B3 is set as the vertebral area L2 And, similarly the vertebral areas L3 and L4 are set. The X-ray image P having the vertebral areas L1-L4 set up as above is sent to the vertebral area setting element 19.

Step S4 (Putting the Area Numbers)

The area number setting element 19 puts an area number to the respective vertebral areas L1-L4 based on the received data. Specifically, the area number L1 is put to the vertebral area L1, and as follows assigns the area number L2-L4 to the respective vertebral areas L2-L4. And the area number setting element 19 superimpose-displays the line-marker designating the areas of the setup vertebral areas L1-L4 (dashed line) and the marker N showing the provided area number to the X-ray image P displayed on the monitor 31 (referring to FIG. 6).

Figure 6:
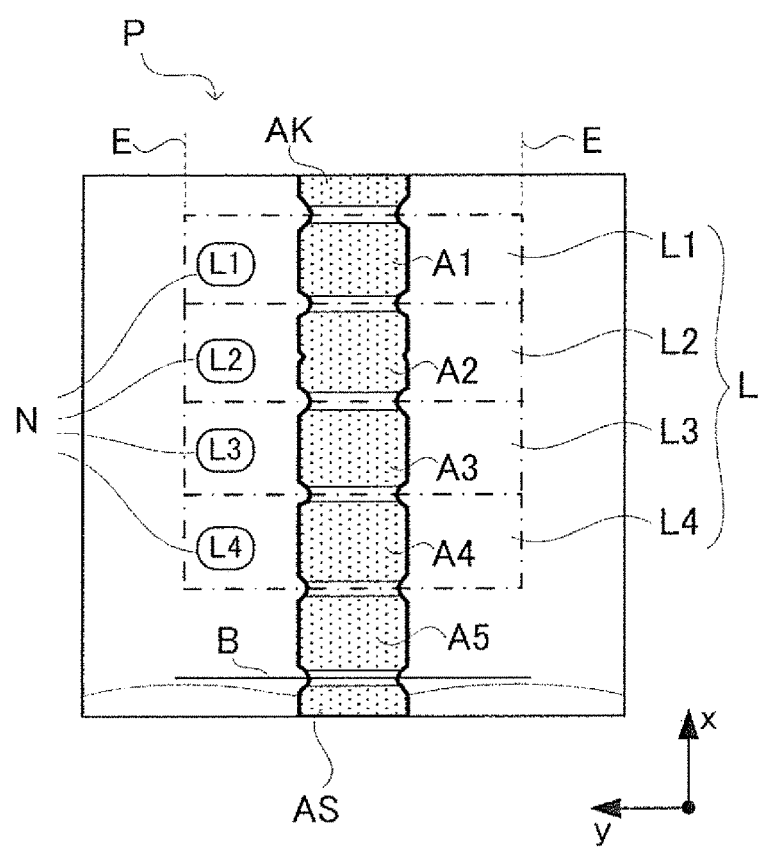
FIG. 6 is a schematic diagram illustrating a process of the Step S4 according to the aspect of the Embodiment.

The operator visually recognizes the vertebral areas L1-L4 superimpose-displayed on the monitor 31 and confirms whether or not the respective setup vertebral areas L1-L4 are accurately enclosing a corresponding vertebra A among the lumbar vertebrae from the first lumbar vertebra A1 to the fourth lumbar vertebra A4. Referring to FIG. 6, when the respective vertebral areas accurately includes the corresponding vertebra A, the operator ends the series of the operations relative to the image processing and performs bone densitometry using the X-ray image P in which the vertebral area L and the area number N are set up.

Figure 7A:
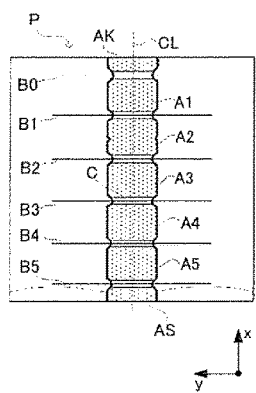
FIG. 7A-FIG. 7C are schematic diagrams illustrating an example of a setting error occurred in the Embodiment relative to vertebral areas.

On the other hand, when the respective vertebral areas L1-L4 are set regardless of an error of setting of the imaging location of the X-ray image P or an error of automatic segmentation processing, the respective vertebral areas L1-L4 may not accurately include the corresponding vertebra. Referring to FIG. 7A, an example of the error-setting relative to the vertebral area L is the case in which the borderline extraction element 15 fails to extract the borderline B (broken line indicated by the sign 130) between the thoracic vertebra AK and the first lumbar vertebra A1. In such case, the vertebral area setting element 17 identifies the borderline B between the first lumbar vertebra A1 and the second lumbar vertebra A2 as the borderline B1, which is the borderline closest to the head of the subject M, and subsequently identifies the borderline B2-B5 in order from the side of the head of the subject M.

Figure 7B:
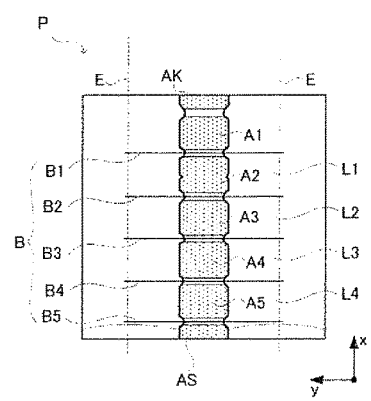

Accordingly, the vertebral area setting element 17 sets the area including the second lumbar vertebra A2 as the vertebral area L1 followed by extracting the areas respectively including the third vertebra A3 to the fifth vertebra A5 as the vertebral areas L2-L4 (FIG. 7B). And referring to FIG. 7C, the area number N actually uncorresponding to the lumbar vertebra is assigned to the vertebral area L. Consequently, when the bone density is analyzed, the accurate bone densitometry can be hardly measured because the vertebral data actually relative to the lumbar vertebra A2 is erroneously used as the vertebral data relative to the lumbar vertebra A1.

Accordingly, when the error setting relative to the vertebral area L takes place, the operation of the step S5 is preformed to correct the location of the vertebral area L. Hereinafter, the inventor sets forth an operation to correct the location of the vertebral area L, which is a characteristic aspect of the image processing device according to the Embodiment. In addition, referring to FIG. 7C according to the Embodiment, the inventor sets forth an example, wherein the state in which the vertebral areas L1-L4 are corresponding to the second lumbar vertebra A to the fifth lumbar vertebra A5 is corrected.

Step S5 (Erase of the Setup Data)

Figure 7C:
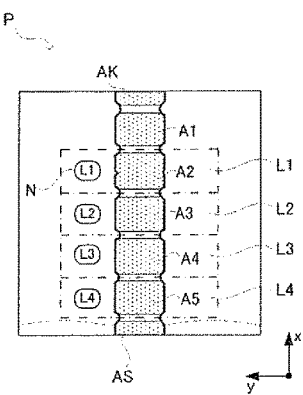
Figure 8A:
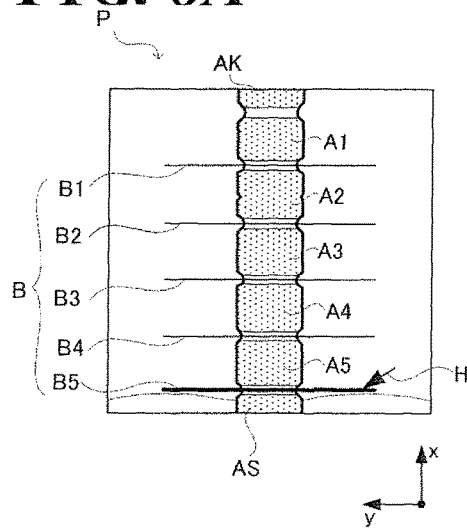
FIG. 8A-FIG. 8D are schematic diagrams illustrating processes of the steps S5-S8 according to the aspect of the Embodiment.

In such case, it is required to correct the state in which the locations of the respective vertebral areas L are as is indicated in FIG. 7C to become the state indicated in FIG. 6. This time, the operator operates the input element 27 to get the mode to correct the vertebral areas. Following shifting to the correction mode, the operator operates the input element 27 to select the borderline B (borderline B5 of the Embodiment) to be shifted relative to the location (FIG. 8A). When the borderline B is selected by the correction mode, a signal relative to the directive contents of correction of the borderline B is sent from the input element 27 to the setup data erase element 21 via the main control element 25.

The setup data erase element 21 erase the setup data based on the received signal. Specifically, the setup data erase element 21 erases the data of the location and the range of the vertebral areas, which are already set up, and the data of the area numbers already assigned to the respective vertebral areas L1-L4. In addition, the timing when the setup data erase element 21 erases the setup data in accordance with receiving the signal relative to the directive content to correct the borderline B is not limited to the above, and the setup data can be erased at which time the mode is changed to the correction mode.

Step S6 (Correction of the Borderline)

Figure 8B:
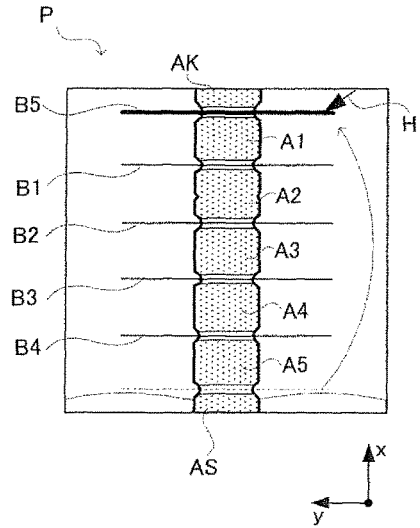

Following erase of the setup data, the operator operates the input element 27 to shift-correct the selected borderline B5 to the predetermined location. Specifically, the borderline B5 shifts to the border (indicated by the sign B0 in FIG. 7A) between the thoracic vertebra AK and the first lumbar vertebra A1 (FIG. 8B). When the borderline B5 shifts to the right location, the correction of the borderline is completed.

Once the vertebral area is set according to the conventional image processing device, each other's locational relationship between the vertebral area and the borderlines are respectively and morphologically correlated and the restriction that is each other's locational relationship between the vertebral area and the borderline and is morphologically determined becomes active. Consequently, the borderline B cannot shift to the location as if at which the specified vertebral areas per se overlap each other. Therefore, according to the conventional device, the borderline B5 cannot move upward to cross over the borderline B4.

In contrast, according to the image processing device of the Embodiment, the setup data erase element 21 erases the data of the vertebral area and the area number in the correction mode. Accordingly, when the borderline B is corrected, the restriction that is the locational relationship between the borderline B and the vertebral area L1 and the borderline B and the area number N and is morphologically determined has been canceled. Consequently, according to the aspect of the Embodiment, the borderline B5 can shift to any location of the X-ray image P.

Step S7 (Resetting of the Vertebral Area)

Following completion of correction of the borderline, the operator operates the input element 27 to input a directive to reset the vertebral areas. The input directive contents are sent to the resetting directive element 23 via the main control element 25. The resetting directive element 23 sends the signal of the directive contents to reset the vertebral area L in accordance with the corrected location of the borderline B to the vertebral area setting element 17.

Figure 8C:
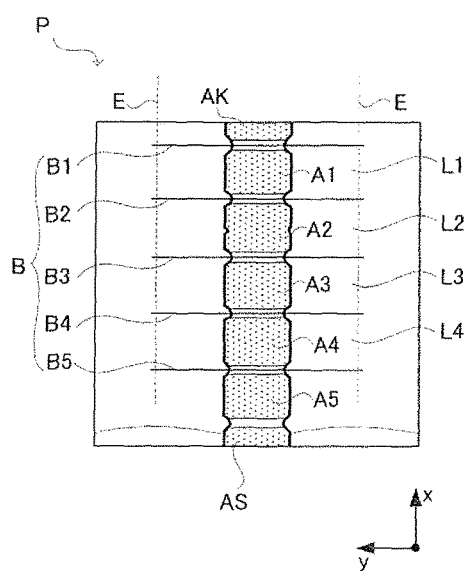

The process in which the vertebral area setting element 17 resets the vertebral area L is the same as the step S3. Relative to the X-ray image having the corrected borderline, the borderline that is located closest to the head of the subject M is the borderline B5 and subsequently the borderline B1-B4 are in the line in turn (FIG. 8B). Consequently, the vertebral area setting element 17 newly specifies the borderline B5 before the correction as the borderline B1 and subsequently the borderline B1-B4 before the correction as the new borderline B2-B5 (FIG. 8C).

Following completion of the respecification of the borderline B, the vertebral area setting element 17 sets newly the vertebral areas L1-L4 based on the respecified borderlines B1-B5. In such case, the respecified borderline B1 is the borderline between the thoracic vertebra AK and the first lumbar vertebra A1 and the respecified borderline B2 is the borderline between the first lumbar vertebra A1 and the second lumbar vertebra A2. Accordingly, the newly setup vertebral area L1 is the area including the first lumbar vertebra A1. Similarly, the respecified vertebral areas L2-L4 are respectively including the corresponding vertebra A from the second lumbar vertebra A2 to the fourth lumbar vertebra A4.

Step S8 (Reputting of the Area Numbers)

Figure 8D:
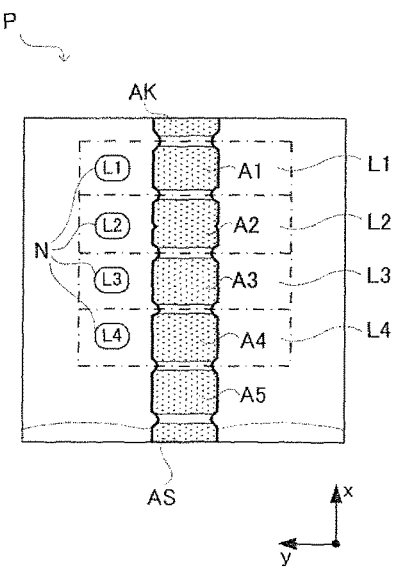

The data of the X-ray image P having the vertebral area L reset as above is sent to the area number setting element 19. The area number setting element 19 reputs an area number to the respective reset vertebral areas L1-L4 based on the receiving data. And the area number setting element 19 superimpose-displays the line designating the areas of the vertebral areas L1-L4 (dashed line) and the marker showing the area number N to the X-ray image P displayed on the monitor 31 (referring to FIG. 8D). The reput area number N accurately represents the vertebra A of the corresponding lumbar vertebra. Consequently, the operator can perform appropriately bone densitometry using the acquired X-ray image referring the automatically displayed area number N and the line denoting the vertebral area L. Accordingly, the locations of all vertebral areas L can be corrected by shifting just one borderline.

The specific operational example of the Step S5-S8 are set forth below. Specifically, the operator operates the mouse consisting of the input element 27 to move the cursor H in the X-ray image P displayed on the monitor 31 to put the cursor H on the borderline B and clicks. The borderline 135 to be corrected is selected by the click operation, so that the setup data erase element 21 can erase the setup data by selecting the borderline B5 (Step S5). The operator moves the borderline B5 to the location of the borderline B0 by dragging (Step S6). Following shifting of the borderline B5 to the adequate location, the signal is sent from the resetting directive element 23 to the vertebral area setting element 17 by the dropping operation and resetting of the vertebral area L and resetting of the area number are executed (Step S7, S8).

Figure 10A:
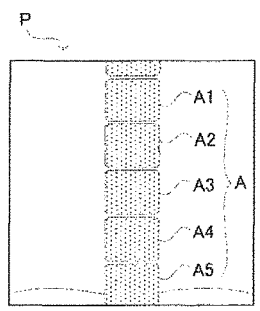
FIG. 10A-FIG. 10E are schematic diagrams illustrating an operation of the image processing device according to the aspect of the conventional Embodiment and problems due to the aspect of the conventional Example.
Figure 10B:
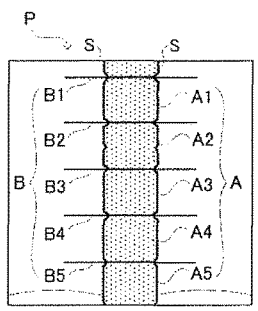
Figure 10C:
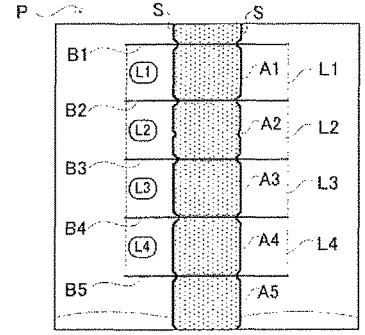
Figure 10D:
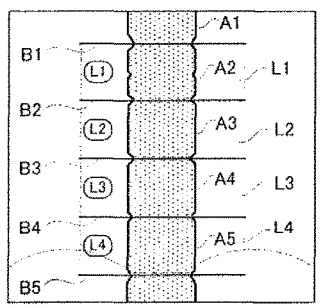
Figure 10E:
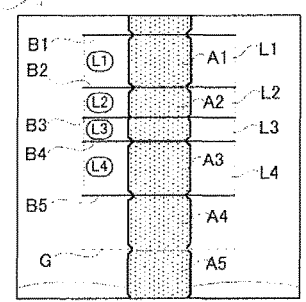

Referring to FIG. 10E, relative to the erroneous setting of the vertebral area L, the other example thereof may be the case in which the borderline B is extracted to the wrong location based on the slight constriction formed on the vertebra A. When the erroneous setting of the vertebral area takes place as referred to the FIG. 10E, the conventional image processing device moves the borderline B to the location G indicated by the sign G, next moves the borderline B4 to the location indicated by the sign B5, and further requires moving of the borderline B3 to the location indicated by the sign B4. On the other hand, according to the image processing device 9, the borderline B3 extracted to the wrong location is selected and the borderline B3 is shifted to the location indicated by the sign G, and subsequently the vertebral area is reset, so that the locations of all vertebral areas L can be corrected. In such way, according to the aspect of the Embodiment, the operational steps required for correction of the vertebral area can be shortened.

Effects of the Aspect of the Embodiment 1

In such way, according to the image processing device of the Embodiment, when the borderline is shift-corrected, the data of the area numbers N and the vertebral areas L are erased by the setup data erase element 21. Subsequently, the resetting directive element 23 directs contents to reset the vertebral area under the condition in which the borderline is shift-corrected. The vertebral area setting element 17 resets the vertebral area L and the area number N based on the location of the corrected borderline B by the directive from the resetting directive element 23.

Figure 11A:
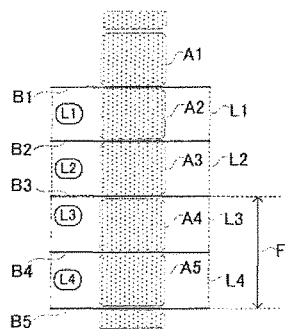
FIG. 11A-FIG. 11C are schematic diagrams illustrating an operation of the image processing device according to the aspect of the conventional Example and problems due to the aspect of the conventional Example.
Figure 11B:
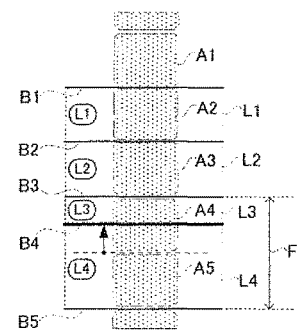
Figure 11C:
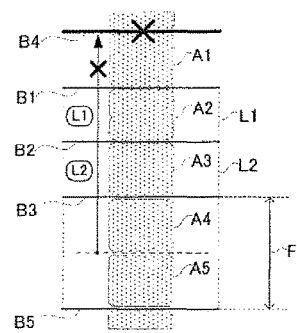
Figure 12A:
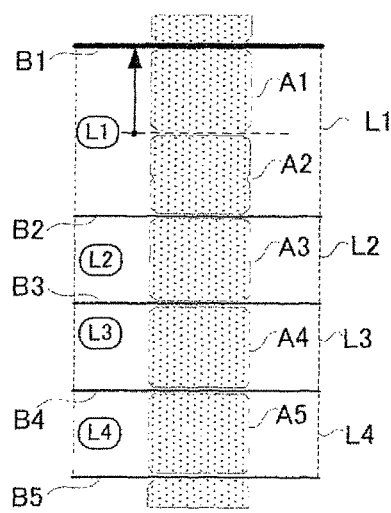
FIG. 12A-FIG. 12D are schematic diagrams illustrating the problematic aspects of the image processing device of the conventional Example.
Figure 12B:
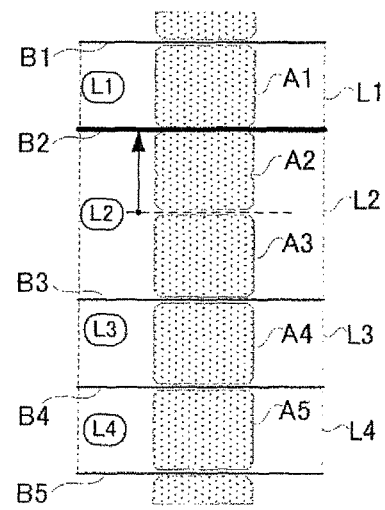
Figure 12C:
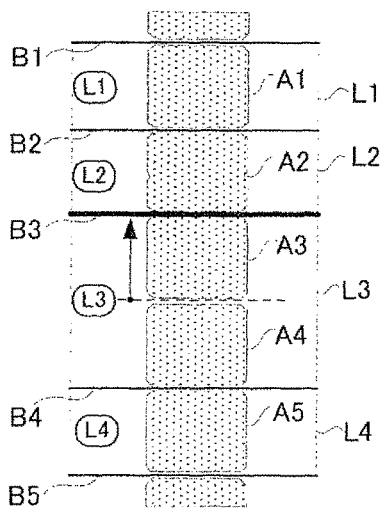
Figure 12D:
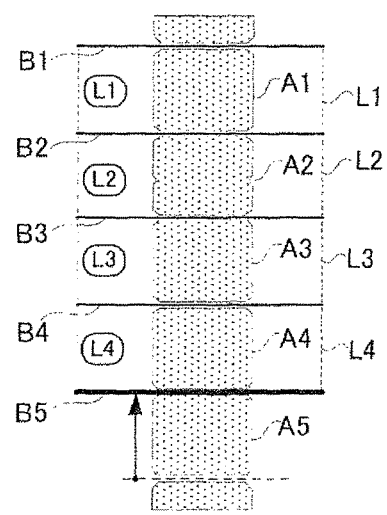

Once the vertebral area is set according to the conventional image processing device, each other's locational relationship between the vertebral area and the borderline are morphologically correlated. For example, the vertebral area L1 is defined as the area sandwiched by the borderline B1 or the borderline B2, the area size of the vertebral area L1 varies in accordance with shift of the borderline B1 or the borderline B2. In such way, the movable range of the borderline is restricted due to the restriction that is a locational relationship between the vertebral area and the borderline and is morphologically determined (referring to FIG. 11).

Therefore, referring to FIG. 7C or FIG. 7D, according to the conventional device, when the locations of the vertebral areas are shifted respectively, all borderlines B1-B5 must be shifted respectively in turn (referring to FIG. 12). As results, a number of the borderlines are needed to be shift-corrected, so that the work-burden of the operator can be heavy. In addition, time needed for the image processing can be long.

On the other hand, the image processing device according to the Embodiment, when the location of the borderline is shift-corrected, the data of the vertebral area, which are already set up, and the data of the area number already put to the vertebral area are erased. In such case, the restriction that is the locational relationship of the correlated vertebral area and borderline and is morphologically determined is canceled due to the erase of the vertebral area, so that the borderline can be shifted to any location. In addition, the data of the vertebral area and so forth are erased, so that it is avoidable that the remained data of the bone area, under the condition in which the restriction is canceled, becomes a drag when the location of the borderline is corrected.

And the respective vertebral areas are set to the right location based on the location of the corrected borderline by the resetting directive to reset the vertebral areas. Specifically, only the borderline extracted to the wrong location is selected and shift-corrected to the right location and correction of the vertebral area can be executed by resetting and directing, so that the number of the borderlines needed to be corrected can be reduced. As results, the work-burden relative to the correction of the vertebral area can be largely lessened.

The present invention is not limited to the aspect of the Embodiments set forth above and another alternative Embodiment can be implemented set forth below.

(1) According to the aspect of the Embodiment 1 as set forth above, a processing to erase the data of the vertebral area L and the data of the area number is executed as a pre-processing to execute the correction of the borderline B is performed, but the present invention is not limited thereto. Specifically, if the processing is a processing to cancel the restriction that is the each other's locational relationship between the respective borderline B1-B5 and the respective vertebral areas L1-L4 and is morphologically determined, the pre-processing to correct the borderline B is not limited to the processing to erase the data of the vertebral area L and the area numbers.

Figure 9A:
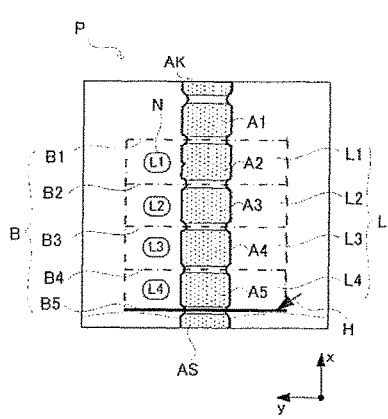
FIG. 9A-FIG. 9C are schematic diagrams illustrating processes of the steps S5-S8 according to the aspect of the alternative Embodiment.
Figure 9B:
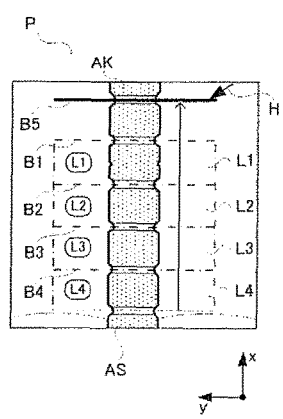

As an alternative Embodiment, referring to FIG. 9A, the setup data erase element 21 cancels the each other's locational relationship correlated in-between the borderline B and the vertebral area L at the step S5 under the condition in which the markers indicating the vertebral area L and the area numbers are being maintained. And the operator operates the input element 27 to shift-correct the borderline B at the step S6 (FIG. 9B). Since the restriction that is the each other's locational relationship between the borderline B and the vertebral areas L and is morphologically determined is canceled, the area size of the vertebral area L and the area numbers related to the vertebral area L are not changed even if the borderline B5 shifts.

Figure 9C:
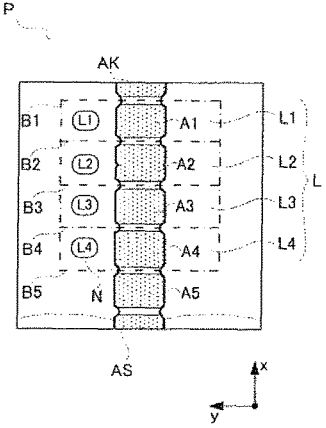

Following completion of the correction of the borderlines, the operator respecifies the borderline B1-B5 based on the locational relationship of the corrected borderline B, and resets the vertebral area L and the area number N at the step S7 and S8 (FIG. 9C). The data of the reset vertebral area L and the area number N are overwritten on the previous data before the correction of the borderline B and superimpose-displayed on the X-ray image P.

According to the aspect of the alternative Embodiment, even when the borderline B is shifted, the locations of the vertebral areas L1-L4 do not vary, so that the respective areas of the vertebral areas L cannot overlap. Specifically, it does not contradict the precondition of the vertebral area in which the vertebrae A are individually segmented due to a change of the location of the borderline B, so that the borderline B can be shift-corrected to any location while displaying the uncorrected original location of the vertebral area L without the correction. The operator can shift-correct the borderline B while referring the uncorrected original vertebral area L and the uncorrected original area number N without the correction, so that the operator can absolutely shift-correct the borderline B to the target location.

(2) According to the aspect of the Embodiment 1 as set forth above, the vertebrae of the lumbar vertebrae are used as target bone tissues for an X-ray imaging, but the bone tissues for the target region are not limited to vertebrae. Specifically, if multiple bone tissues are the regions connected in a line, the aspects of the present invention can be applied. An example of the bone tissues connected in a line is a bone of limb finger.

(3) According to the aspect of the Embodiment 1 as set forth above, the inventor sets forth as the subject M is decubitus, but the subject M can be erect according to the aspect of the present invention.

REFERENCE OF SIGNS

1 X-ray imaging apparatus
5 X-ray tube
7 FPD
9 Image processing device
13 Image generation element (Image generation means)
15 Borderline extraction element (Borderline extraction means)
17 Vertebral area setting element (Bone area setting means)
19 Area number setting element (Area number setting means)
21 Setup data erase element (Setup data erase means)

23 Re-setting directive element (Re-setting directive means)
25 Main control element
27 Input element (Correction directive means, borderline correction means)

Also, the inventors intend that only those claims which use the complete words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An image processing device, comprising:
   an image generation means that generates an X-ray image, the X-ray image projecting multiple concatenate bone tissues relative to a subject;
   a borderline extraction means that extracts a borderline between said adjacent bone tissues in said X-ray image;
   a bone area setting means that sets an area sandwiched by said adjacent borderlines as a bone area;
   a correction directive means that inputs a correction directive to correct a location of said borderline;
   a setup data erase means that cancels a restriction that is an overlap of respective locational relationships between the bone area and the borderlines and is morphologically determined based on the correction directive input to the correction directive means;
   a borderline correction means that shift-corrects said borderline to any location of said X-ray image under a condition in which said restriction is canceled by said setup data erase means; and
   a resetting directive means that inputs a resetting directive for resetting said bone area to said bone area setting means based on the location of said borderline corrected by said borderline correction means under a condition in which said borderline correction means shift-corrected said borderline.

2. The image processing device, according to claim 1, wherein:
   said setup data erase means erases the data of said bone area, based on said correction directive that is input by said the correction directive means; and
   wherein said bone area setting means sets up said data.

3. The image processing device, according to claim 1, wherein:
   an area number setting means that provides an area number to distinguish said respective bone areas relative to said respective bone areas; and
   wherein said setup data erase means that cancels a restriction that said overlap of the locational relationship between said bone area and said borderlines and is morphologically determined based on said correction directive that is input to said correction directive means.

4. The image processing device, according to claim 1, wherein:
   said bone tissues are vertebrae.

* * * * *